United States Patent [19]

Roland

[11] Patent Number: 5,173,272

[45] Date of Patent: Dec. 22, 1992

[54] HEATED CONVEYOR AND PROCESS FOR DISINFECTING SIZE-REDUCED HOSPITAL REFUSE

[76] Inventor: Rolf E. Roland, Hauptstrasse 57, D-6688 Illingen, Fed. Rep. of Germany

[21] Appl. No.: 654,602

[22] PCT Filed: Aug. 2, 1989

[86] PCT No.: PCT/EP89/00904

§ 371 Date: Mar. 1, 1991

§ 102(e) Date: Mar. 1, 1991

[87] PCT Pub. No.: WO90/01340

PCT Pub. Date: Feb. 22, 1990

[30] Foreign Application Priority Data

Aug. 8, 1988 [DE] Fed. Rep. of Germany ....... 8810087

[51] Int. Cl.$^5$ ............................................. A61L 2/06
[52] U.S. Cl. ...................................... 422/295; 422/26; 422/299; 422/304; 198/561; 198/720; 34/216; 34/217; 34/218
[58] Field of Search ................. 422/26, 295, 299, 304; 71/9, 14, 901; 198/720, 561; 34/216, 217, 218

[56] References Cited

U.S. PATENT DOCUMENTS

| | | | |
|---|---|---|---|
| 1,324,758 | 12/1919 | Baker | 198/561 |
| 4,058,364 | 11/1977 | Terumoto | 422/304 |
| 4,142,304 | 3/1979 | Ricci et al. | 198/561 |
| 4,816,231 | 3/1989 | Stenström et al. | 422/304 |
| 4,979,347 | 12/1990 | Shibauchi et al. | 422/304 |

Primary Examiner—Robert J. Warden
Assistant Examiner—Laura E. Collins
Attorney, Agent, or Firm—Collard & Roe

[57] ABSTRACT

A heated conveyor for disinfecting contaminated, size-reduced hospital refuse comprises a scraping conveyor with two endless link chains (1,2) to which drives (6) are fastened. The scraping conveyor is arranged in a housing with electricially heated floor and walls which is closed with the exception of an upper inlet opening (17), an outlet opening (19) and an air vent (18). In the disinfection process implemented by this conveyor compressed saturated steam is injected into the housing through steam nozzles.

8 Claims, 1 Drawing Sheet

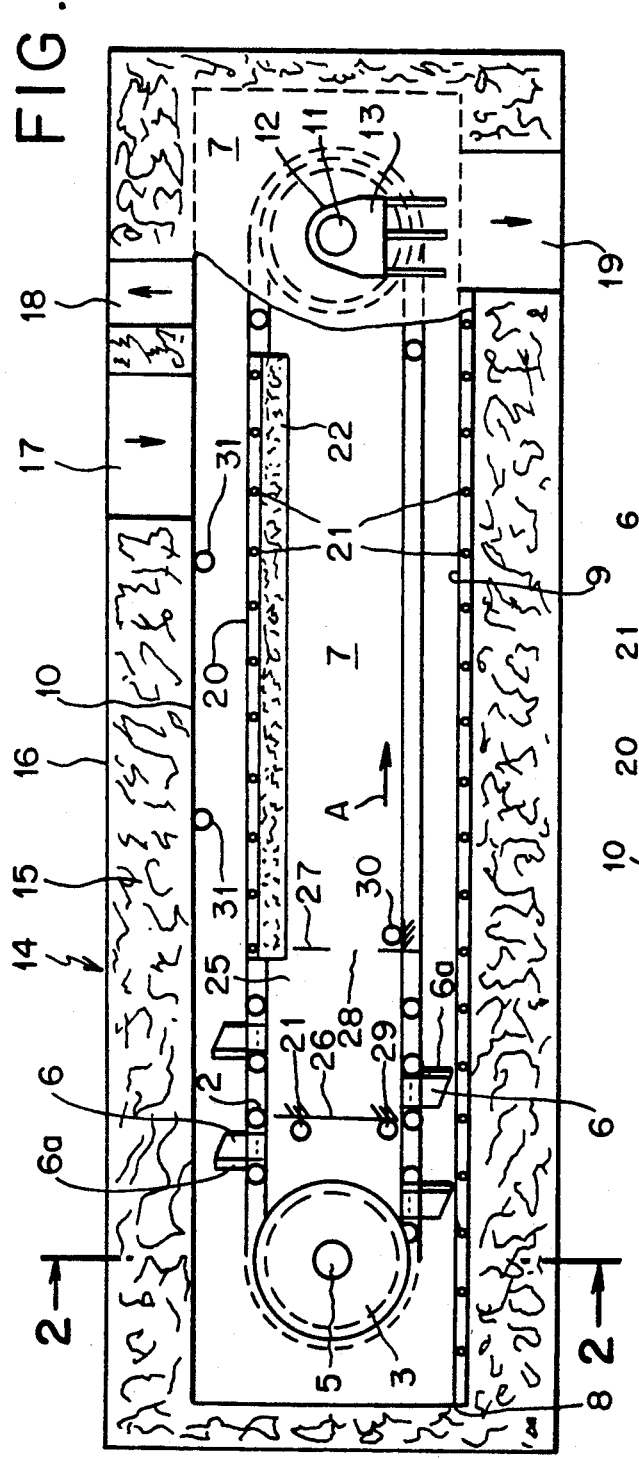
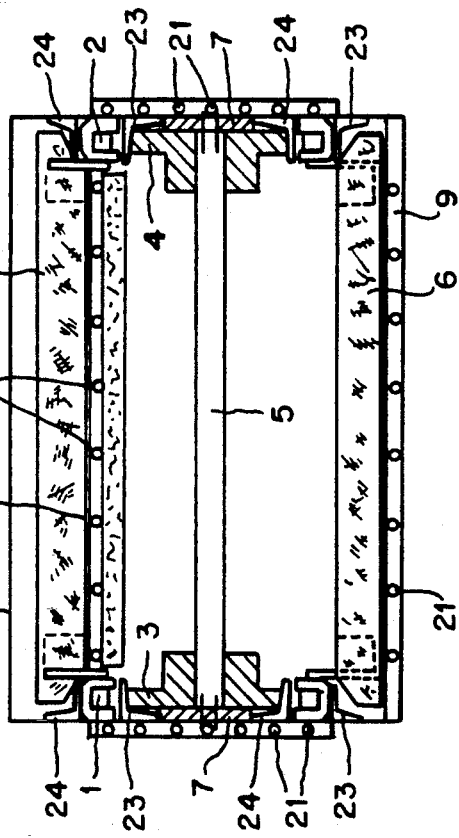

HEATED CONVEYOR AND PROCESS FOR DISINFECTING SIZE-REDUCED HOSPITAL REFUSE

BACKGROUND OF THE INVENTION

The invention concerns a heated conveyor and a process for disinfecting contaminated size-reduced hospital refuse. A familiar conveyor of this kind consists of 2 conveyor screws contrarotating in 2 open half shells, the walls of the half shells being heated with heat transfer oil. The twin screw conveyors are arranged inside a housing provided with an inlet opening, an outlet opening and an air vent (German Utility Model 87 02 503) The use of screw conveyors has proved to be disadvantageous in operation inasmuchas the throughput capacity of such disinfecting facilities does not come up to expectations. The material to be disinfected is displaced laterally by the rotating movement of the spirals, causing piling-up and rendering the contact surfaces of the heated walls of the half shells ineffective. Adequate disinfection can only be maintained if the transport velocity is kept so low that a sufficiently short period of dwell can be obtained. Furthermore, the use of heat transfer oil to heat the conveyor raises environmental issues, be it the problem of the disposal of waste oil, leakages or the formation of noxious vapours during overheating.

SUMMARY OF THE INVENTION

It is, thus, the object of the invention to provide a heated conveyor and a process for disinfecting contaminated size-reduced hospital refuse with an improved disinfection performance and throughput capacity.

This object is achieved according to the invention inasmuch as the conveyor consists of a so-called scrape conveyor with two endless link chains, to which flight attachments are secured, that the scrape conveyor is arranged in a housing whose base and long side walls can be heated by means of electric resistance heating and which is closed with the exception of an upper inlet opening, an exit opening and an air vent, that a drop shaft into which compressed, saturated steam can be injected is formed by two vertical sheet metal plates and that the sheet metal plate positioned downstream possesses an overflow opening.

The object is furthermore achieved by a process for disinfecting according to the invention.

The use of a scrape conveyor with rotating flight attachments, well-proven in the field of mechanical conveying and handling, eliminates the problem of the material to be handled piling up, which could lead to the heated contact surfaces becoming exposed. Heating the base and the long side walls of the housing with electric resistance heating is not only ecologically beneficial but also offers a possibility of adjusting and switching off filamanent energy quickly.

Separate regulation of the heating elements means, too, that the heat balance within the conveyor can also be kept constant in an advantageous manner.

The formation of a drop shaft, through which the material being fed in falls onto the base plate and the fact that the material is heated and moistened in the drop shaft already with compressed, saturated steam means that disinfection is begun or prepared in the drop shaft. The sheet metal plate with its overflow opening positioned down stream of the drop shaft causes that part of the material in the drop shaft which is stripped by the flight attachments of the lower belt of the link chains and sent in the direction of the conveyor to be rotated and fall down onto the heated base plate through the overflow opening.

In the inventive process, compressed, saturated steam, free of condensate, is used, preferably at a temperature of 140 degrees Celsius. The temperature of the base is adjusted in an embodiment so that it is below that of the compressed, saturated steam being employed; the temperature of the side walls is chosen in such a way that it is either at least equal to or in excess of that of the superheated steam.

The temperature at the base should preferably not exceed a range lying between 119 and 125 degrees Celsius. Preference is given to the use of steam at 140 degrees Celsius; the temperature of the side walls in this case is preferably 150 degrees Celsius.

The inventive process makes periods of dwell of up to 15 minutes possible of the material to be disinfected. Shorter periods of dwell, e.g. of 10 minutes, can be attained, depending on the nature of the contamination involved.

To ensure undisturbed movement of the link chains upon their guideways, it is expedient that the guideways of the link chains be protected by guards from hospital refuse falling onto them.

A further measure, designed to improve the efficiency of the heated conveyor, consists, according to the invention, in the fact that a heatable intermediate plate which starts below the inlet opening and ends in the area of the drop shaft, is arranged below the path of motion of the flight attachments of the upper belt of the link chains, the inlet and outlet openings lying almost on top of one another. This solution not only brings about the required circulation of the material to be treated; it also causes a considerable increase in the heated contact surface over which the material to be treated is fed—and that with a scraping conveyor of the same length, by way of comparison. Additional steam nozzles can be provided above the intermediate bottom.

As hospital refuse contains on a large scale articles made of plastic, which releases harmful gaseous substances upon being heated, in order to ensure that the housing is sealed as hermetically as possible it is provided with an air vent with a filter; the driving axle of the guide wheels of the link chains nearest to the outlet opening is placed outside the housing and sealed by glands vis-a-vis the side walls, whereas the other axle is fixed to the side walls of the housing on the front side and the guide wheels of the axle are pivoted on the axle.

The flight attachments of the link chains preferably are provided with a layer consisting of temperature-resistant rubber or plastic, as the flight attachments drag against the wall of the base, and possibly against the intermediate plate, while they are in motion.

Finally, in order to prevent heat losses, it is necessary to surround the housing with an outer casing, into which a thermal insulation is incorporated, this outer casing being provided with inlet and outlet openings and an air vent. It is expedient to provide the top part of the outer casing with a snap closure, so that disturbances can be removed rapidly.

BRIEF DESCRIPTION OF THE DRAWINGS

In the drawing a form of construction of the subject matter of the invention is shown by way of example.

FIG. 1 shows a vertical cross-section, a diagrammatic representation, with an outer casing providing thermal insulation, and FIG. 2 shows a profile, in accordance with line II—II in FIG. 1, without the outer casing.

DETAILED DESCRIPTION OF THE PREFERRED EMBODIMENT

First the scrape conveyor is described, which comprises 2 endless link chains 1, 2, which run upon guide wheels 3, 4 and carry flight attachments 6, arranged at intervals from one another, which are provided with a coating 6a of temperature-resistant rubber. The guide wheels 3, 4 are pivotally supported on the non-driving axle 5, whose front end is fixed by screws to the long side walls 7 of a housing, which, in addition to the short side wall 8, also possesses a base 9 and a top 10. The scraping conveyor is driven by means of an axle 11, located outside the housing in bearing brackets 12, the latter being supported by bracket pin 13 fixed to one of the side walls 7.

The housing, comprised of side walls 7, 8, the base 9 and the top 10, is surrounded by a outer casing 14, into which a heat insulation 15 made of mineral wool with an aluminum-laminated coating is incorporated. The top 16 of the outer casing 14 can be removed easily by means of a snap closure (which is not shown). The top 16 of the outer casing 14 has an inlet opening 17 so that the size-reduced hospital refuse can be fed into the appliance, a gas discharge opening 18, to which a tube with a filter (not shown) is attached and an outlet opening 19. The inlet opening 17 and the outlet opening 19 lie almost on top of one another in the case of the heatable conveyor shown in FIG. 1. It goes without saying that all the openings in the outer casing 14 have corresponding openings in top 10 and in the base 9 of the housing.

Below inlet opening 17 an intermediate bottom 20 in the shape of a shallow box-like construction begins, into which heating rods 21 of a resistance heating are installed. Below the heating rods 21, the intermediate bottom 20 contains a thermally insulating layer 22. The intermediate bottom 20 extends between link chains 1, 2 and is secured at the upper angles 23 (FIG. 2), which are fixed to the side walls 7 of the housing and serve to steer the link chains 1, 2. The link chains are protected from above by means of such angles 24, too.

The intermediate bottom 20 extends as far as the area of the filling shaft 25, which is formed by the vertical sheet metal plates 26 and 27. The side wall 27 arranged down stream in the direction of arrow A has an overflow opening 28 near the lower belt of the link chains 1, 2. Behind the sheet metal plate 26 are tubes 29, which are linked up to a steam generating plant (not shown) and equipped with steam nozzles, which inject the superheated steam into the drop shaft 25. A further tube 30 carrying superheated steam is provided next to the sheet metal plate 27, to handle the material being transported along the base 9 in the direction of arrow A. Base 9 and the side walls 7 are also in the shape of a box and contain heating rods 21. Tubes 31, through which steam is sent, are provided with steam nozzles above the intermediate bottom 20.

The mode of operation of the described appliance is as follows: The size-reduced hospital refuse is fed into the device via inlet opening 17 and falls onto the heated intermediate bottom 20, onto which the material is fed by the flight attachments 6 of the upper belt of the link chains 1, 2 of the scraping conveyor, which is operated extremely slowly.

After this first treatment stage, the material falls into drop shaft 25 and onto the heated base 9, where it is transported by the flight attachments in the direction of the arrow A to the outlet opening 19. In the drop shaft 25 the material is heated up and moistened once more, by means of compressed, saturated steam provided by the steam nozzles in the tubes 29. Part of the material to be found in drop shaft 25 can overflow via the overflow opening 28 in sheet metal plate 27 and also fall down while rotation is being carried out, the steam nozzles of tube 30 continuing to inject compressed, saturated steam. The disinfected material is led to a pressing station (which is not depicted here) via outlet opening 19.

In a simpler version of the device the intermediate bottom 20 is missing and the inlet opening 17 is arranged above drop shaft 25. The size-reduced hospital refuse arrives at the heated base 9 directly via the drop shaft. It goes without saying that because of the arrangement of the baffles, in particular in the drop shaft 25, repeated reshuffling of the material to be treated can be achieved. Arrangements can also be made to put steam pressure above atmospheric into service in the housing of the conveyor. In this case the waste air opening 18 must be provided with an indicator showing excess pressure and the inlet and outlet openings 17 and 19, respectively, equipped with valves.

I claim:

1. Heated conveyor for disinfecting contaminated, size-reduced hospital refuse, comprising
    a scraping conveyor having two endless link chains;
    flight attachments secured to each endless link chain;
    a housing in which the scraping conveyor is arranged, said housing having a top, a base and long side walls;
    means for electric resistance heating of said base and said long side walls;
    said housing being closed with the exception of having an upper inlet opening in the top, having an outlet opening in the base and having an air vent in the top;
    a drop shaft being formed by two vertical sheet metal plates said vertical sheet metal plates being attached to said scraping conveyor;
    steam nozzles positioned within said drop shaft for injecting compressed, saturated steam into said drop shaft; and
    one of said vertical sheet metal plates being downstream and the other vertical sheet metal plate being upstream, said sheet metal plate positioned upstream having an overflow opening.

2. The heated conveyor according to claim 1,
    wherein said link chains have guideways; and wherein said guideways each have a protecting cover.

3. The heated conveyor according to claim 1,
    wherein a heatable intermediate bottom is positioned below a path of motion of the flight attachments of an upper belt of the link chains; said upper belt begins below the upper inlet opening and ends in the area of the drop shaft; and
    said upper inlet opening and said outlet opening are aligned almost on top of one another.

4. The heated conveyor according to claim 3, comprising
    additional steam nozzles provided over the heatable intermediate bottom.

5. The heated conveyor according to claim 1, further comprising
a driving axle for guide wheels of the link chains positioned nearest to the outlet opening;
means for supporting the driving axle outside the housing and for sealing the driving axle opposite the side walls of the housing by means of glands;
another axle being fixed onto the sidewalls of the housing at a front end by means of guide wheels; and
said guide wheels being supported on another axle.

6. The heated conveyor according to claim 1, wherein the flight attachments have a temperature-resistant coating of either rubber or plastic.

7. The heated conveyor according to claim 1, further comprising
an outer casing for surrounding the housing;
a thermal insulation in said outer casing; and
said outer casing provided with an inlet opening and an outlet opening and an air vent.

8. The heated conveyor according to claim 7, further comprising
a cover equipped with a snap closure for said outer casing.

* * * * *